United States Patent [19]

Gutierrez et al.

[11] 4,163,393
[45] Aug. 7, 1979

[54] VOID DETECTOR SYSTEM

[75] Inventors: Manuel Gutierrez, Golden; Phillip F. Enger, Arvada, both of Colo.

[73] Assignee: The Unites States of America as represented by the Secretary of the Interior, Washington, D.C.

[21] Appl. No.: 931,069

[22] Filed: Aug. 4, 1978

[51] Int. Cl.$^2$ ............................................. G01N 29/04
[52] U.S. Cl. ......................................... 73/584; 73/12; 73/588
[58] Field of Search .................... 73/12, 584, 588, 594, 73/649, 579, 582

[56] References Cited

U.S. PATENT DOCUMENTS

| | | | |
|---|---|---|---|
| 3,361,225 | 1/1968 | Nichols | 73/588 |
| 3,762,496 | 10/1973 | Milberger et al. | 73/588 |
| 3,888,108 | 6/1975 | Brands | 73/12 |
| 3,937,065 | 2/1976 | Milberger et al. | 73/588 |
| 3,946,598 | 3/1976 | Towne et al. | 73/579 |

Primary Examiner—Charles A. Ruehl
Attorney, Agent, or Firm—Thomas Zack; Donald A. Gardiner

[57] ABSTRACT

An apparatus for non-destructively testing concrete comprises a tri-wheel platform having a transducer mounted adjacent each wheel and mechanically coupled to the concrete to be responsive to vibration. An aperture is formed in the center of the platform equispaced from the three transducers. Vibrations are imparted to the concrete that emanate outwardly toward the transducers by manually striking the concrete through the center aperture with a rubber tipped impact rod. The transducers generate electrical signals responsive to the amplitudes of detected vibrations which are a function of the structural continuity of the concrete. Electronic circuitry monitors the outputs of the transducers and makes comparisons of the signals to determine whether a flaw exists in the concrete within the region bounded by the three transducers.

24 Claims, 9 Drawing Figures

$T_1$ = TRIGGER FROM PHOTOCELL TO START RAMP GENERATOR
$T_2$ = SAMPLE SIGNAL AND INTEGRATE
$T_3$ = HOLD SAMPLE
$T_4$ = RESET

VOID DETECTOR SYSTEM

TECHNICAL FIELD

The present invention relates generally to methods of and apparatus for testing concrete, and more particularly, to a method of and apparatus for non-destructively testing concrete by impacting the concrete and monitoring induced vibrational energy using a triangular array of transducers equispaced from the point of impact.

BACKGROUND ART

To help prevent failure in the foundation of water carrying utilities, it is necessary to know the conditions of concrete substructures, both existing and under development. The structural integrity of the concrete is also determined as an indicium of acceptance and as a safety assurance measurement for soundness of structural support.

In the prior art of which we are aware, non-destructive testing of concrete is made by impacting the concrete to induce vibrations and then measuring the magnitude of vibrations at positions on the concrete spaced apart from the point of impact. For example, Brands U.S. Pat. No. 3,888,108, issued on June 10, 1975, discloses a pavement testing apparatus including a mallet that is adapted to impact the pavement and an accelerometer spaced apart from the mallet to monitor vibrations in the pavement at a single position spaced apart from the mallet. The mallet and accelerometer are both carried within a small, portable container that rests on the pavement surface.

Another type of pavement testing apparatus is disclosed in Milburger et al. U.S. Pat. No. 3,762,496, issued on Oct. 2, 1973, wherein a tri-wheel cart contains a metal-pegged wheel that successively taps the pavement as the cart is wheeled, and induced vibrational energy in the pavement is monitored by transducers at two of the wheels. The transducer wheels and pavement tapping wheel are positioned on a common axis.

While the prior art apparatus for testing pavement of which we are aware have been generally satisfactory for limited applications, these apparatus are not suitable for monitoring very fine voids or discontinuities behind concrete linings and at concrete separations because the single transducer or linear transducer array does not provide adequate sensitivity. Fine voids or discontinuities in concrete substructures for heavy-duty applications, such as water carrying utilities, tend to grow under pressure and fail after a period of time. Also, testing a substantial concrete area using the prior art apparatus of which we are aware requires a substantial testing period since only a small area of the concrete is monitored at any time by the single transducer or linear transducer array.

Accordingly, one object of the invention is to provide an improved method of and apparatus for testing concrete that is responsive to very fine structural defects.

Another object is to provide an improved method of and apparatus for testing concrete wherein the concrete is monitored with a relatively wide field of view so that a large area of concrete can be scanned in a relatively short period of time.

Another object is to provide a new and improved method and apparatus, wherein concrete is non-destructively tested by impacting the concrete to induce vibrations and monitoring vibrational energy in the concrete using an array of three transducers equispaced from the point of impact.

Another object is to provide a method of and apparatus for non-destructively testing concrete, wherein a portion of the concrete is impacted to induce vibrations and vibrational energy in the concrete is monitored by an array of transducers mechanically coupled to the concrete and positioned in a triangular array with the point of impact of the concrete being equispaced from the transducers.

Another object is to provide a method of and apparatus for non-destructively testing concrete, wherein a portion of the concrete is impacted to induce vibrations, and vibrational energy in the concrete is monitored by first, second and third transducers oriented in a triangular array; and vibration responsive signals generated by the transducers are mutually compared, with any imbalance among the signals being characteristic of a void or discontinuity in the concrete.

Another object is to provide a new and improved apparatus for testing concrete that is portable, easy to position over a test region and adapted for use in confined areas of the types typically encountered at water carrying utilities.

DISCLOSURE OF INVENTION

An apparatus for non-destructively testing concrete comprises a triangular platform supported on the concrete by a set of three wheels positioned, respectively, at the platform corners. Piezoelectric vibration transducers mounted on the platform above the wheels are mechanically coupled to the concrete through the wheels. The transducers generate electrical signals in response to vibrational energy in the concrete coupled through the wheels. The platform contains a central aperture through which a test portion of the concrete is exposed. A rubber-tipped rod is provided for impacting the concrete through the platform aperture.

Vibrational energy in the concrete emanating outwardly from the point of impact is received by the transducers, the transducer signals being supplied to an electrical circuit that simultaneously samples the three signals and then stores the signal magnitudes for mutual comparison. The common mode signal portions are rejected so that only differences in signal magnitudes between one and the other two of the transducers are supplied to an output circuit. The output circuit comprises a pair of analog meters that are selectively switched in circuit to display defect dependent signal magnitude differences among the three transducers. The transducer signals are also monitored and compared to a threshold voltage which, when exceeded, is independently indicative of a defect in the concrete. A visual of audible alarm is triggered to indicate the presence of any defect.

Stray vibrations in the platform are isolated from the vibration transducers by resilient members positioned between the platform and the wheels. The stray vibrations are also isolated from the sensors by sampling circuitry that is synchronized to the impact rod as the rod projects through the platform aperture to strike the concrete.

The platform carries all electronic circuitry required for monitoring the transducers and generating the results. An elongated handle is pivotally connected to the platform to enable the apparatus to be freely transported along the concrete to be tested. The platform is formed of sections that are hinged together to enable the platform to be lowered through a narrow opening, such as a manhole, for access to a test area.

Still other objects and advantages of the present invention will become readily apparent to those skilled in this art from the following detailed description, wherein we have shown and described only the preferred embodiment of the invention, simply by way of illustration of the best mode contemplated by us of carrying out our invention. As will be realized, the invention is capable of other and different embodiments, and its several details are capable of modifications in various obvious respects, all without departing from the invention. Accordingly, the drawings and description are to be regarded as illustrative in nature, and not as restrictive.

BEST MODE FOR CARRYING OUT THE INVENTION

Figures 1, 4:
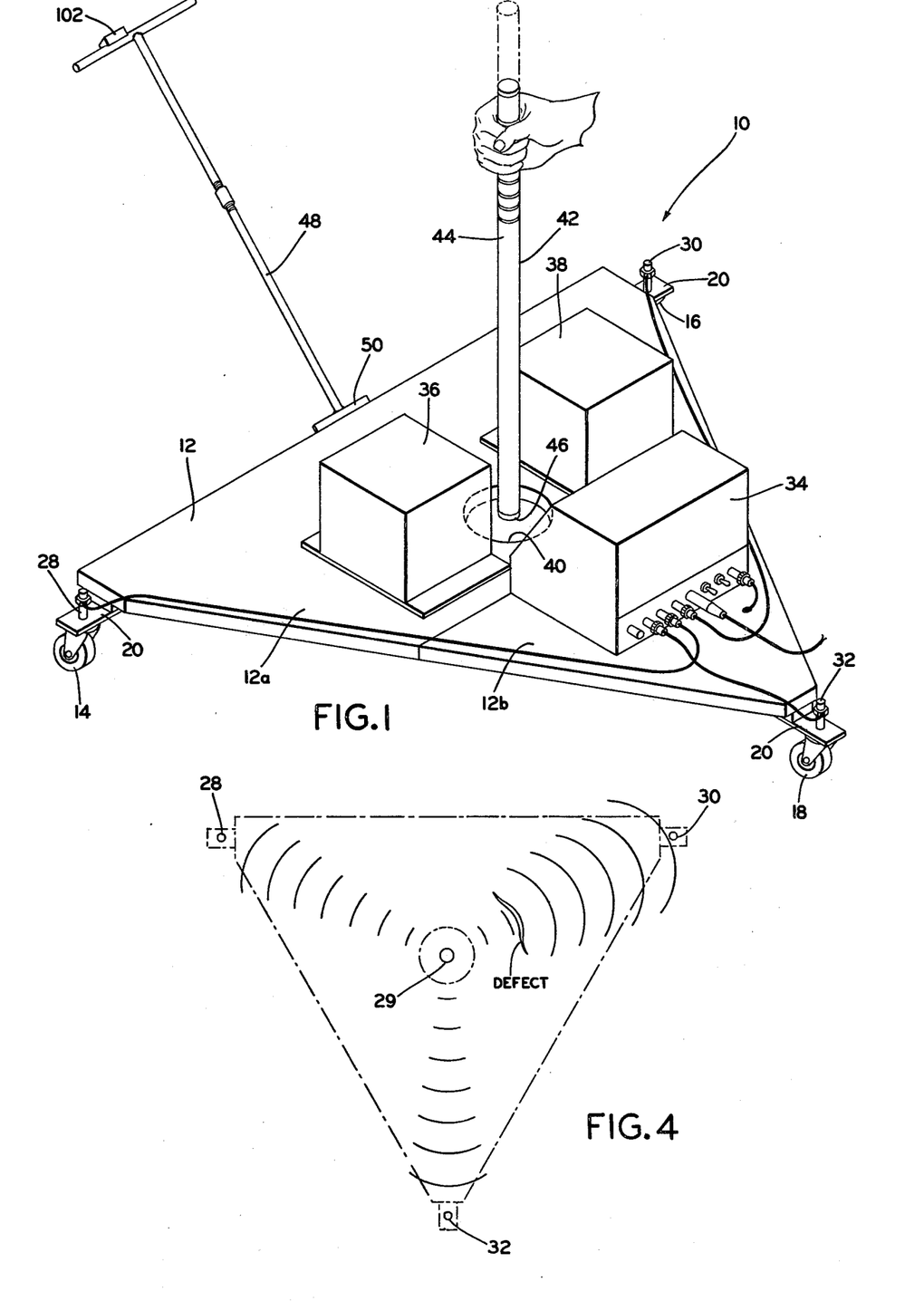
FIG. 1 is a perspective view of the apparatus of the present invention showing the upper surface of the platform and operation of the impact rod during testing.
FIG. 4 is a symbolic drawing showing propagation of vibrational energy through concrete in a test region bounded by the three transducers.
Figures 2, 3:
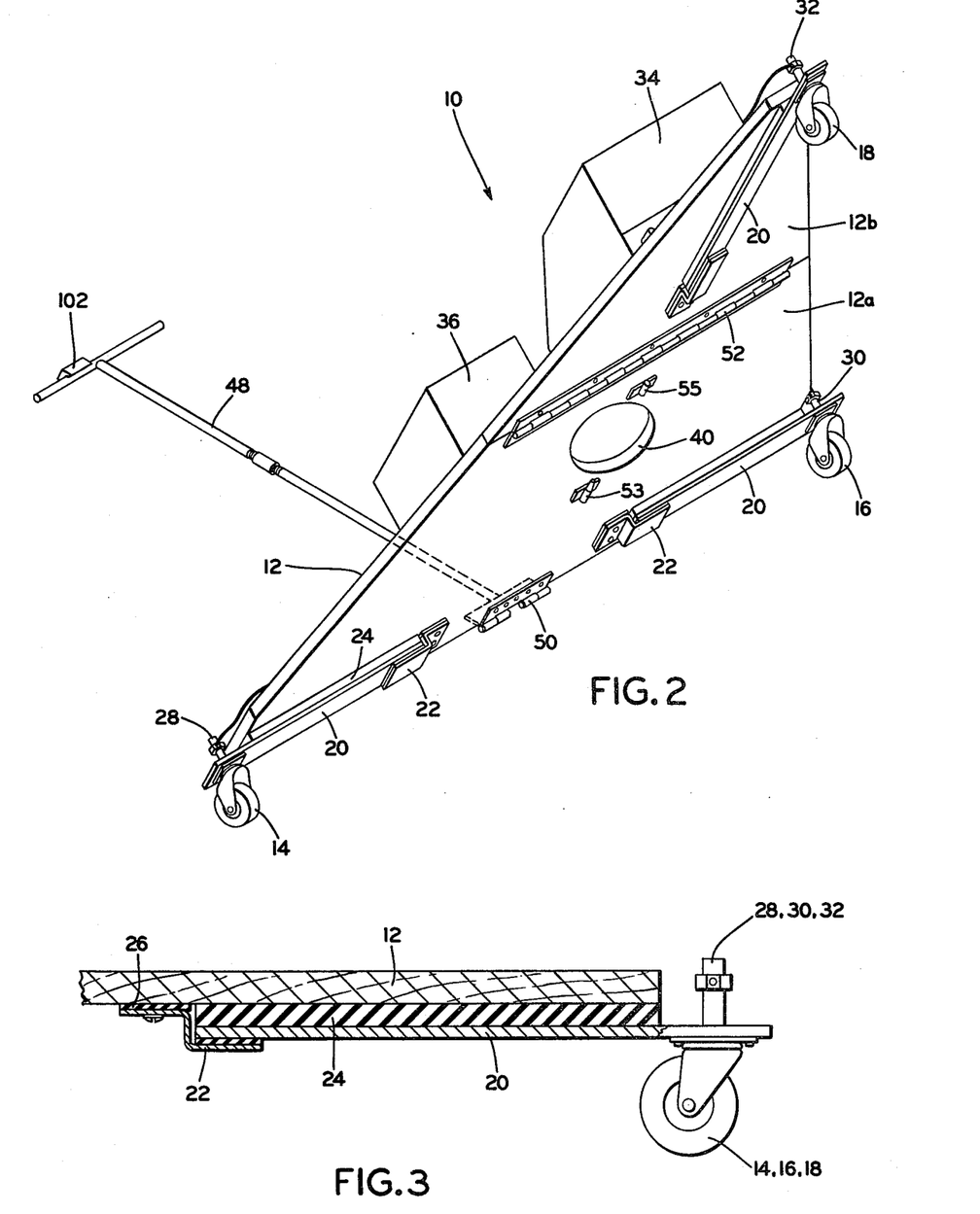
FIG. 2 is another perspective view of the apparatus exposing the lower surface of the platform to show the lamp and photocell pair as well as platform hinge.
FIG. 3 is a cross-sectional side view of a portion of the apparatus showing one set of the resilient members for mechanically isolating a vibration transducer from the platform.

Referring initially to FIGS. 1 and 2, an apparatus 10 for non-destructively testing concrete comprises a generally triangular platform 12 having corners at which wheels 14, 16 and 18 are located for supporting the platform on the concrete to be tested. The wheels 14, 16 and 18 form caster assemblies that are mounted respectively to mounting bars 20 (see FIG. 3) secured to platform 12 by brackets 22 but mechanically isolated from the platform by vibration absorbing members 24 and 26 formed of rubber or other resilient material.

Above each wheel 14–18 on bar 20 is a conventional vibration responsive transducer or accelerometer 28, 30 and 32. The positions of the transducers 28, 30, 32 define an equilateral triangle, which when projected onto the concrete establishes what is termed hereinafter "test region". Transducers 28–32 are prestressed onto bars 20 so as to be responsive to vibration impacted to the bar through the wheels 14–18. Wheels 14–18 are formed of a rigid material, such as metal, to provide maximum coupling of vibrational energy from the concrete to transducers 28–32. The transducers 28–32 are electrically connected to signal processing circuitry, described hereinafter, housed within a cabinet 34. The cabinet 34, as well as battery packs 36 and 38, is supported on the platform 12.

An aperture 40 is formed in the center of the platform 12 equispaced from the transducers 28–32. A portion of concrete to be tested is exposed through the aperture 40 to be impacted by a rod 42 having a metal body 44 and rubber tip 46. An elongated handle 48 is attached to one side of the platform 10 at hinge 50 to enable the platform to be transported and positioned on the concrete at a location undergoing testing. The hinge 50 enables the handle 48 to be pivoted to a vertical position for lowering the platform 12 through a restricted opening, such as a manhole, into the test location. Another hinge 52 (FIG. 2) attached to platform 12 enables platform sections 12a and 12b to be folded for lowering into a manhole and also for storage.

In accordance with the invention, the presence or absence of voids or discontinuities in concrete within a region bounded by transducers 28–32 is determined by locating the platform 12 so that the transducers surround the region of concrete to be tested, striking or impacting the concrete through the aperture 46 using the rod 42 and then measuring vibrational energy in the concrete at the transducers. Vibrational energy propagates omnidirectionally through the concrete from the point of contact in the manner represented schematically in FIG. 4. The magnitude of the vibrational energy received by the transducers 28–32 is a function of (1) the intensity of impact, (2) the thickness of the concrete, (3) the damping factor of the transducers 28–32 and the damping factor of the specimen under test. Variables (1)–(3) are maintained constant during a test, so that any difference in induced vibrational energy (amplitude or duration) detected by any of the transducers compared to the energy detected by the remaining transducers is generally a function of only an anisotropic damping factor in the concrete caused by a defect.

We have found that a void or discontinuity in the concrete is characterized by vibrational energy having higher amplitude and/or longer signal duration received by one of the transducers compared to that received by the remaining two transducers. This characteristic is illustrated in FIG. 4, wherein the vibrational energy emanating toward transducer 30 from point of impact 29 has a higher energy content, that is, a larger amplitude and duration, than that vibrational energy emanating toward the remaining two transducers 28 and 32. In accordance with the invention, the outputs of transducers 28–32 are simultaneously sampled during each test initiated by striking the concrete with rod 42. During a sample interval, the signal generated by each transducer 28–32 is amplified and integrated to provide a signal that is a function of vibrational energy in the concrete (dependent on both magnitude and time duration). The integrated transducer signals are then supplied to a differential circuit which is an analog subtraction circuit that compares the signal generated by forward transducer 32 with the signal generated by transducer 28 and also with the signal generated by transducer 30 to generate two difference signals. Any imbalance in the magnitude of the integrated signal from transducer 28 or from transducer 30 relative to transducer 32, characterized by a nonzero difference signal, is displayed on a pair of analog meters to indicate that a void or discontinuity probably exists in the test region. Depending on the relative positions of the two analog meters, the approximate location of a fault within the test region can be determined.

A block diagram of the electronic circuitry described above is shown in the block diagram of FIG. 5. The outputs of transducers 28, 30 and 32 are supplied to identical signal processing circuits each comprising a high input impedance amplifier 54, a sampling circuit 56 and an integrator 58. The outputs of integrators 58 are supplied to conventional differential circuits (analog subtractors) 60 and 62 that control analog meters 64 and 66 for indicating any signal imbalances between the signal generated by transducer 32 and the signals generated by the remaining transducers 28 and 30. The outputs of integrators 58 are also connected to a conventional window detector circuit 67 through a diode circuit 68. The window detector 67 generates an alarm signal to lamp 70 and speaker 72 if any of the integrator signals are outside an upper and lower limit preselected by the operator (in a manner described below) during a test interval. A digital voltmeter 74 is also connected to the output of the diode circuit 68 to display the magnitude of the maximum voltage generated by any of the integrators 58 and appearing at the cathodes of the diodes.

Figure 5:
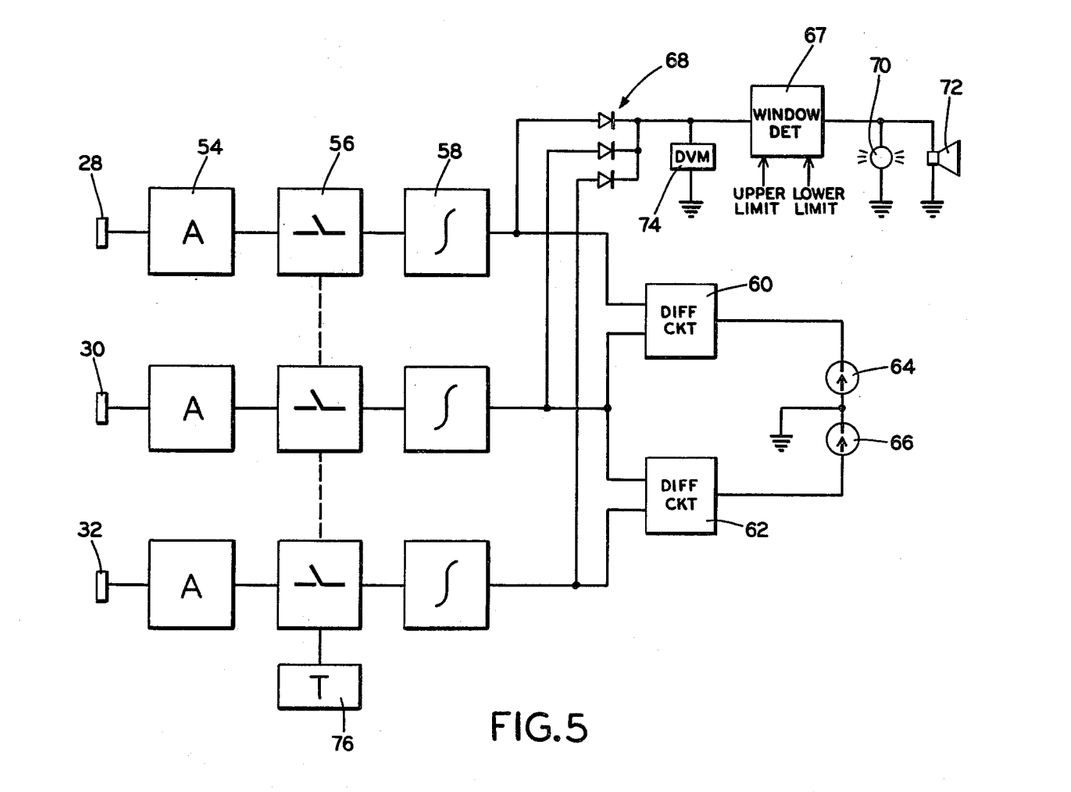
FIG. 5 is a block diagram of the circuitry for processing the transducer signals.

The output of each amplifier 54 is sampled by the sampling circuit 56 under the control of timing circuit 76. The timing circuits 76 control sampling of all three sampling circuits 56 simultaneously to eliminate synchronization problems among the three signal processing circuits.

Figure 6:
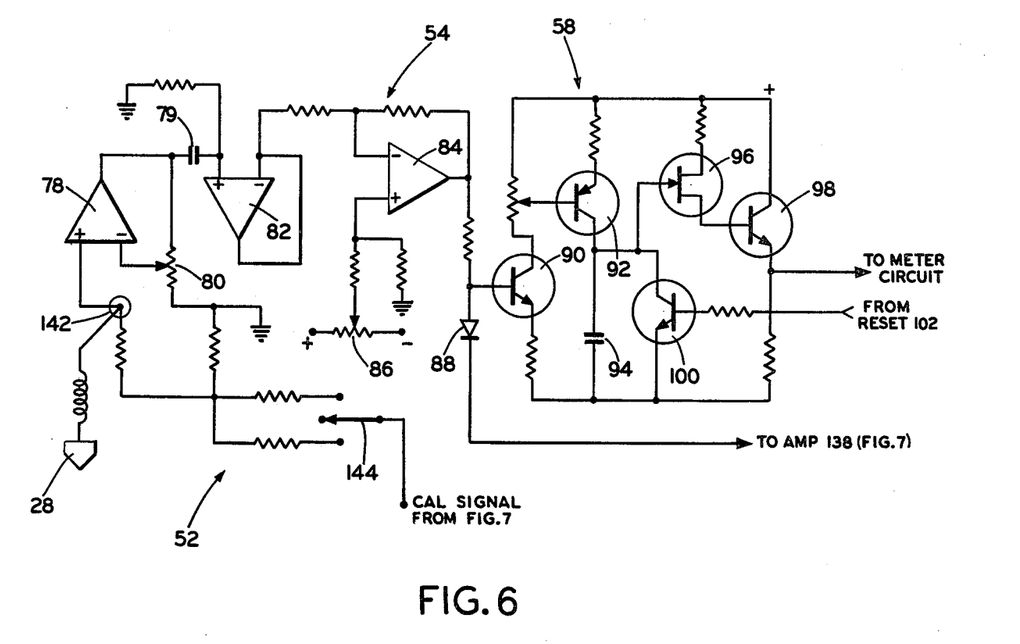
FIG. 6 is a schematic diagram of a circuit for amplifying and processing the transducer signals.

Referring to FIG. 6 showing the amplifier circuit 54 and integrator circuit 58 in detail, the output of transducer 28 is connected to input terminal 142 of amplifier 54 (it is to be understood that identical circuits are connected to and operate with the remaining transducers 30 and 32, but only the transducer 28 circuit is described for brevity). Transducer 28 is connected to a first operational amplifier 78 which amplifies the transducer signal in accordance with an amplification factor determined by gain control 80. The output of amplifier 78 is supplied through a decoupling capacitor 79 to a buffer amplifier 82 which in turn supplies the amplified transducer signal to another operational amplifier 84. Any DC offset voltage in the transducer signal is compensated by a balance control 86 (the output of amplifier 84 corresponds to the output of amplifier block 54 in FIG. 5). Diode 88 connected at the output of amplifier 84 controls readout of the amplified signal to transistor 90 which constitutes the input stage of integrator 58. The diode 88 thus functions as sampling gate 56 in FIG. 5. The signal generated by transducer 28 is supplied to integrator 58 only when the cathode of diode 88 is high; the transducer signal being shunted when the cathode is low. The sampling voltage at the cathode of diode 88 is controlled by the timing circuit 76 described in detail in connection with FIGS. 7 and 8 below.

Transistor 90 further amplifies the signal generated by amplifier 84 and supplies the amplified signal to another transistor 92 that supplies a current to capacitor 94 which is proportional to the voltage generated by amplifier 84. A ramp voltage appearing across capacitor 94 is a function of the time integral of current through capacitor 92 over a time interval controlled by the sampling period. The ramp voltage developed across capacitor 94 is supplied to an output circuit comprising a field effect transistor 96 and a bipolar transistor 98 controlled in a Darlington configuration to drive differential circuits 60, 62 (FIG. 5). A transistor 100 connected across capacitor 94 is provided to reset the capacitor to zero in response to a reset signal applied to the base of the transistor. The reset signal is manually initiated from a reset control 114 mounted on the platform handle 48 at 102 (see FIG. 1).

Figure 7:
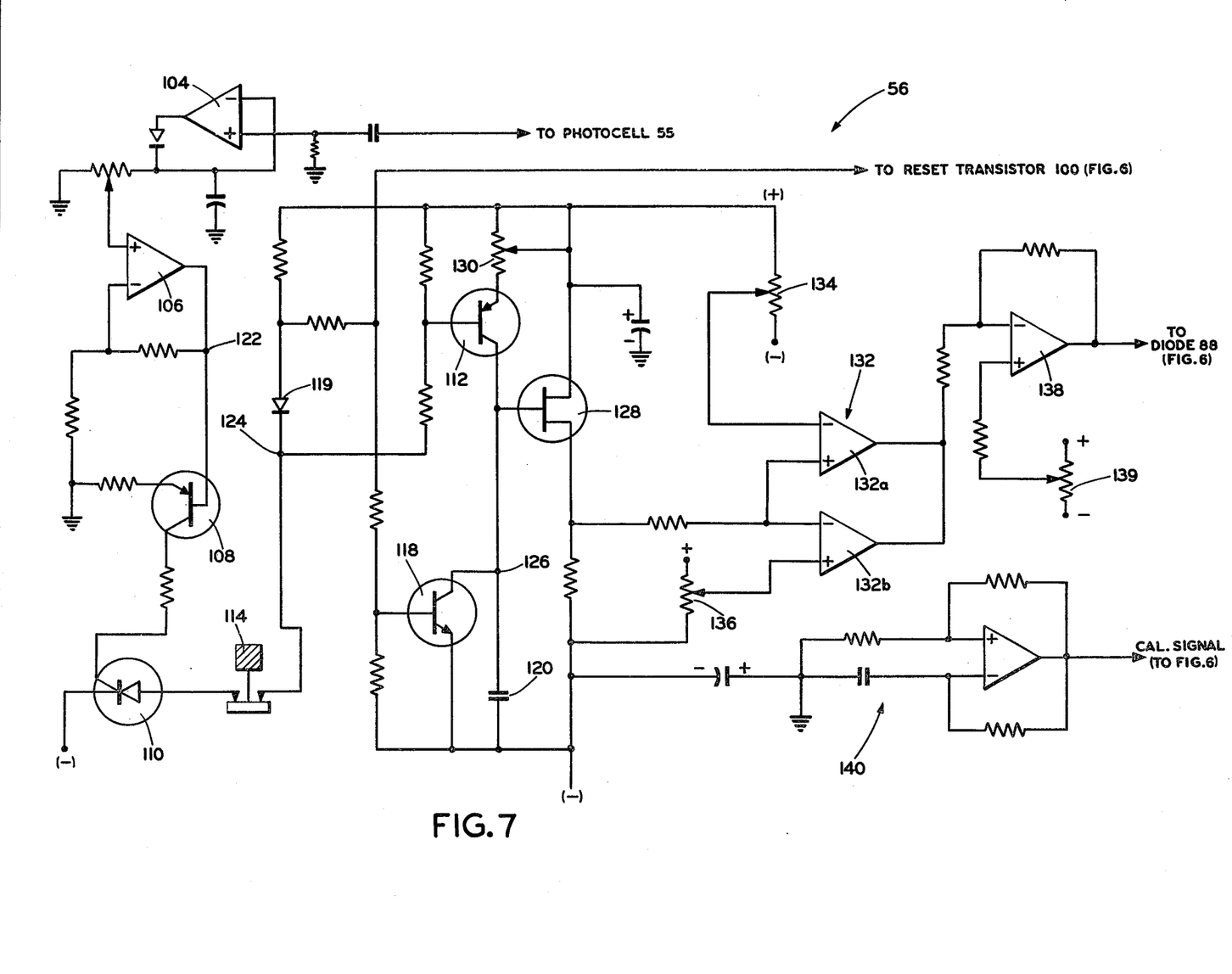
FIG. 7 is a schematic diagram of a timing and sample logic circuit for sampling the transducers signals synchronously to the impact rod.
Figure 8:
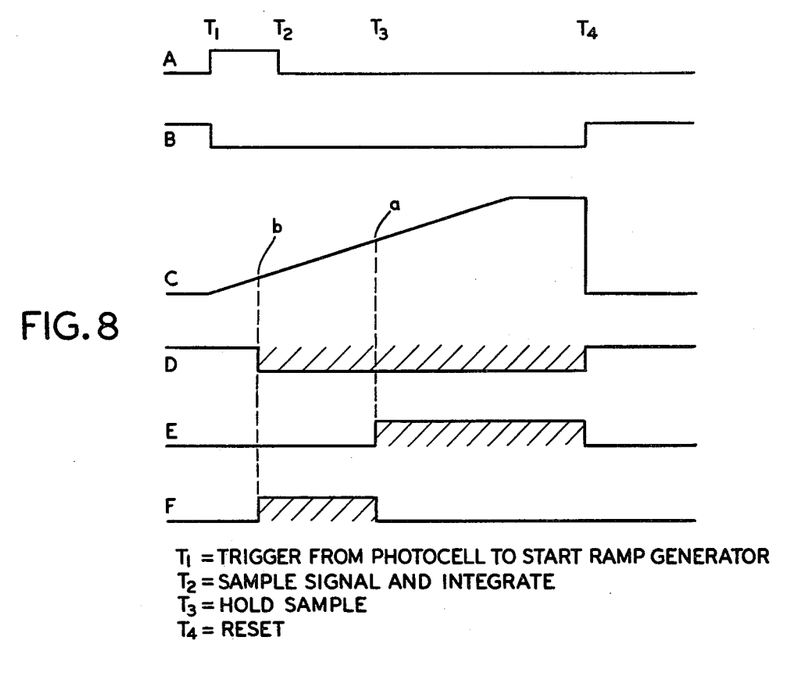
FIG. 8 shows signal waveforms for explaining the operation of the timing and sample logic circuit shown in FIG. 7.

Referring to FIG. 7, sample timing circuit 56 is shown in detail. Synchronization of circuit 56 to operation of impact rod 44 is provided by photocell 55 which generates a signal to amplifier 104 when a light beam projected by lamp 53 to photocell 55 (FIG. 2) is broken by the rod as it is thrusted through platform aperture 40. The trigger signal developed by amplifier 104 is supplied to another amplifier 106 which controls drive to the base of transistor 108. The output of transistor 108 in turn supplies a control signal to the gate of an SCR 110 which is turned on to establish a DC conduction path between the base of transistor 112 and the SCR through a manually operated, normally closed, reset switch 114. SCR 110 is latched in the on state by DC current flowing through the SCR; the latching characteristic of SCR 110 maintains it on until the current flowing through the SCR is interrupted by opening manual reset switch 114. When SCR 110 is on, the base of transistor 112 is driven toward a negative potential applied at the cathode of the SCR by a negative bias supply (not shown) to turn transistor 112 on. Simultaneously, transistor 118 is turned off by the negative drive applied to its base through SCR 110 an diode 119. With transistor 118 off, its collector is driven positive to enable charging of capacitor 120 through transistor 112. This operation is illustrated in FIG. 8 by waveforms A–C, wherein $T_1$ identifies the time at which the photocell 55 generates a trigger signal, with waveform A appearing at node 122 (FIG. 7), waveform B appearing at node 124, and waveform C appearing at node 126. The slope of the ramp signal shown in FIG. 8C is controlled by potentiometer 130 and is applied to the gate of FET 128. The purpose of FET 128 is to isolate the ramp generator transistors 112 and 118 from a conventional window comparator circuit 132 composed of comparators 132a and 132b.

Window comparator 132 develops the sample time by monitoring the ramp signal and (1) opening a sample gate as the ramp signal intersects a lower threshold voltage and then (2) closing the gate as the ramp signal intersects a higher threshold voltage. The lower threshold voltage is established by potentiometer 136, the upper threshold level being developed by potentiometer 134. The sample gate control signal is supplied to diode 88 (FIG. 6) through an inverting amplifier 138 and balance control 139.

The operation of window comparator circuit 132 is shown in FIG. 8 by waveforms C–F. Lower trigger shown in waveform D is developed by comparator 132b in response to the lower threshold voltage identified by b at $T_2$ in waveform C. Similarly, the upper threshold voltage a at $T_3$ generated by comparator 132a is shown in waveform E. The sample time signal shown in waveform F extending between $T_2$ and $T_3$ is developed at the output of amplifier 138 to be supplied to the cathode of diode 88 in FIG. 6. Manual reset via switch 114 (FIG. 1) is at $T_4$.

Again referring to FIG. 7, an oscillator 140 is provided for generating an AC test signal for calibrating amplifier 54 shown in FIG. 6. The AC test signal generated by oscillator 140 is supplied to input terminal 142 of the amplifier through a two-position attenuator 144.

The oscillator 140 is used for initial calibration of the apparatus as well as for maintenance.

Figure 9:
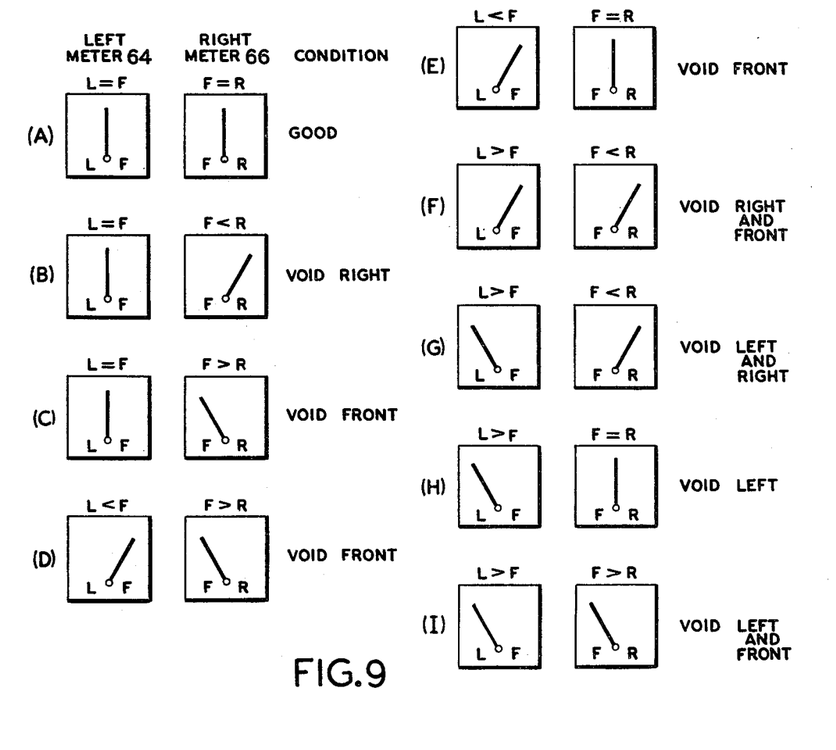
FIG. 9 is a diagram showing various analog meter displays together with interpretations.

Referring again to FIG. 5, the outputs of integrators 58 are supplied to analog comparator of differential circuits 60 and 62 which may be standard differential amplifiers that drive analog meters 64 and 66 in the manner shown in FIG. 9. Differential circuit 60 drives meter 64 corresponding to the output of left hand side, rear transducer 28 (see FIG. 1) compared to the output of front transducer 32 whereas meter 66 monitors the output of right hand side, rear transducer 30 relative to the output of front transducer 32. The meter pairs shown in FIG. 9 show the nine possible outputs A–I from the meters indicating whether or not a void or other defect exists within the region bounded by the transducers 28–32. For example, output A shows a balanced readout on meter 24 and also a balanced readout on meter 66. The vibrational energy detected by transducer 28 is therefore equal to the energy detected by transducer 32. Likewise, the vibrational energy detected by transducer 30 is equal to energy detected by transducer 32. Since the vibrational energy received by each transducer is equal, no void or discontinuity within the test region is considered to exist. In output B, meter 64 has a balanced readout, whereas meter 66 is skewed toward the right. Meter 64 indicates that the vibrational energies received by transducers 28 and 32 are equal to each other, whereas a greater amount of vibrational energy is received by transducer 30 then by transducer 32. A void or discontinuity or other structural defect is therefore presumed to exist in the concrete within the test region, but the void or discontinuity is closer to transducer 30 than it is to the remaining transducers. Similarly, the remaining outputs C–I indicate, as shown in the labels, whether or not a void exists within the test region and whether the void or defect is located within the left, right or front portion or portions of the test area bounded by the three transducers. In some instances when meter readouts are equal, a void may still exist in the test region, e.g., where delays in propagation times of vibration energy to the transducers are equal, due to a large defect. Here, the presence or absence of a defect is determined by the voltmeter 74 which monitors maximum signal level and by window detector 67 which operates alarms 70 and 72 in response to a detected signal outside the threshold level limits.

Of particular importance, the meter readouts shown in FIG. 9 display differences in vibrational energy received by front transducer 32 compared to the vibrational energies received by the remaining two transducers 28, 30. Since the common mode signals generated by integrators 58 are effectively canceled out by differential circuits 60, 62, the system of the present invention is much more sensitive with respect to small defects in concrete than prior art systems of the type wherein only absolute, vibration dependent signals are supplied to a readout or alarm circuit. Furthermore, the triangular test region defined by the three transducers 28–32 enables monitoring of a larger area for each position of the mobile platform than prior art systems using one or two transducers do.

In this disclosure, there is shown and described only the preferred embodiment of the invention, but, as aforementioned, it is to be understood that the invention is capable of use in various other combinations and environments and is capable of changes or modifications within the scope of the inventive concept as expressed herein.

We claim:
1. An apparatus for non-destructively testing concrete, comprising:
 a platform;
 first, second and third vibration receiving transducers on said platform defining the corners of an equilateral triangle, said transducers being mechanically coupled to the concrete being tested and generating vibration responsive electrical signals;
 means for imparting vibration to the concrete at a position equispaced from said transducers; and
 means responsive to said electrical signals for indicating a condition of the concrete within an area bounded by said transducers.

2. The apparatus of claim 1, wherein said platform contains an aperture located at a position equispaced from said transducers, and said vibration imparting means includes means for contacting the concrete through said aperture.

3. The apparatus of claim 2, wherein said contacting means includes a rod having a tip for striking the concrete.

4. The apparatus of claim 3, wherein the tip of said rod is formed of rubber.

5. The apparatus of claim 2, wherein said indicating means includes circuit means for sampling the transducer signals; means for comparing the magnitude of one of the transducer signals individually with the magnitudes of the remaining two transducer signals; and means for displaying results of the comparisons.

6. The apparatus of claim 5, wherein said contacting means includes a rod having a tip adapted to strike the concrete through the platform aperture, said indicating means further including means for monitoring the presence of said rod within said aperture, and said circuit means includes means for synchronizing said signal sampling means to said monitoring means.

7. The apparatus of claim 6, wherein said monitoring means includes a lamp and photocell pair positioned on said platform adjacent said aperture.

8. The apparatus of claim 5, wherein said indicating means includes analog meter readout means, and means responsive to said comparing means for driving said meter means to indicate the results of said comparisons.

9. The apparatus of claim 5, wherein said indicating means further includes circuit means responsive to said transducer signals for detecting the largest of the three transducer signals developed during a sample period, and readout means for displaying the magnitude of said largest transducer signal.

10. The apparatus of claim 5, wherein said indicator means further includes circuit means for generating a threshold voltage, means for comparing the magnitudes of said transducer signals to the magnitude of said threshold voltage, and means for generating an alarm when the magnitude of any of said transducer signals is greater than the magnitude of said threshold voltage.

11. The apparatus of claim 10, wherein said alarm means includes signal lamp means for indicating a void or discontinuity in the concrete.

12. The apparatus of claim 10, wherein said alarm means includes an audible signal for indicating a void or discontinuity in the concrete.

13. The apparatus of claim 5, wherein said transducers are connected to input circuit means, and said indicating means includes means for generating a calibration signal simulating the transducer signals to said input circuit means.

14. The apparatus of claim 1, wherein said platform is mounted on wheels, and said transducers are located, respectively, above said wheels, mechanical coupling of said transducers to the concrete being established through said wheels.

15. The apparatus of claim 14, including means for isolating said transducers from stray vibrations induced in said platform.

16. The apparatus of claim 15, wherein said wheels are secured to mounting bars, and said isolating means includes resilient means disposed between said bars and said platform.

17. The apparatus of claim 16, wherein said platform is triangular, with said wheel mounting bars extending outwardly from the corners of said platform.

18. The apparatus of claim 14, including an elongated handle pivotably attached to said platform to enable pushing of said platform to a test region.

19. The apparatus of claim 18, wherein said platform includes hinge means for folding said platform to enable passage of said platform through a narrow opening to a test region.

20. A method of detecting the presence or absence of structural defects in concrete, comprising the steps of positioning first, second and third vibration receiving transducers in an equilateral triangle array and into mechanical contact with the concrete to be tested, with a test region being bounded by said transducers; inducing vibration into the concrete by impacting the concrete at a location equispaced from said transducers, monitoring vibration responsive electrical signals generated by said transducers; and correlating said signals to a presence or absence of structural defects in the concrete within the test region.

21. The method of claim 20 wherein said structural defects include voids or discontinuities located in the concrete.

22. The method of claim 20 wherein said step of monitoring includes the step of simultaneously sampling the output signals of said transducers, and said step of correlating includes the steps of selectively comparing a first one of said transducer signals with the remaining two transducer signals, and selectively displaying the results of said comparing steps.

23. The method of claim 22, wherein said step of inducing vibrations includes the step of striking the concrete with a rod, and the step of sampling includes the steps of detecting the presence of the rod during striking and synchronizing the step of sampling to the detecting step.

24. The method of claim 20, wherein the step of monitoring includes the steps of monitoring a maximum signal generated by said transducers; generating a reference voltage, comparing said maximum signal to said reference voltage and selectively generating an alarm signal in response to said comparing step.

* * * * *